(12) United States Patent
Jacquot et al.

(10) Patent No.: US 7,847,110 B2
(45) Date of Patent: Dec. 7, 2010

(54) METHOD FOR PRODUCING OPTIONALLY SUBSTITUTED METHYLENEDIOXYBENZENE

(75) Inventors: Roland Jacquot, Francheville (FR); Jean-Roger Desmurs, Communay (FR)

(73) Assignee: Rhodia Chimie, Aubervilliers (FR)

( * ) Notice: Subject to any disclaimer, the term of this patent is extended or adjusted under 35 U.S.C. 154(b) by 834 days.

(21) Appl. No.: 11/587,293

(22) PCT Filed: Apr. 19, 2005

(86) PCT No.: PCT/FR2005/000954

§ 371 (c)(1), (2), (4) Date: Jun. 25, 2007

(87) PCT Pub. No.: WO2005/108385

PCT Pub. Date: Nov. 17, 2005

(65) Prior Publication Data
US 2008/0021228 A1     Jan. 24, 2008

(30) Foreign Application Priority Data
Apr. 20, 2004   (FR) .................................. 04 04168

(51) Int. Cl.
*C07D 317/48*   (2006.01)

(52) U.S. Cl. ...................................................... 549/434
(58) Field of Classification Search ................. 549/362, 549/434
See application file for complete search history.

(56) References Cited

FOREIGN PATENT DOCUMENTS

| EP | 0261977 A2 | 3/1988 |
|---|---|---|
| EP | 0271091 A1 | 6/1988 |

OTHER PUBLICATIONS

Li et al., Montmorillonite clay catalysis. Part 14. A facile synthesis of 2-substituted and 2,2-disubstituted 1,3-benzodioxoles, Journal of the Chemical Society, Perkin Trans., 1998, pp. 3561-3564, No. 21.
International Search Report Issued in PCT/FR 2005/000954 pm Sep. 19, 2005.

*Primary Examiner*—Taofiq A Solola
(74) *Attorney, Agent, or Firm*—Buchanan Ingersoll & Rooney PC

(57) ABSTRACT

The invention relates to a method for producing optionally substituted methylenedioxybenzene. The invention particularly relates to the production of methylenedioxybenzene. The inventive production method is characterized by the fact that it involves the reaction of an optionally substituted catechol with an aldehyde in the presence of a solid acid catalyst selected among: a titanium silicalite and a zeolite that is doped with tin and/or titanium.

47 Claims, No Drawings

METHOD FOR PRODUCING OPTIONALLY SUBSTITUTED METHYLENEDIOXYBENZENE

This application is an application under 35 U.S.C. Section 371 of International application Number PCT/FR2005/000954 filed on Apr. 19, 2005.

The present invention relates to a method for producing optionally substituted methylenedioxybenzene.

More specifically, the invention relates to a method for producing optionally substituted methylenedioxybenzene according to a method which uses a heterogeneous catalyst.

The invention relates more particularly to the production of methylenedioxybenzene.

In the following disclosure of the present invention, the term "optionally substituted methylenedioxybenzene" is intended to mean a compound of methylenedioxybenzene type in which the benzene ring bears a substituent and/or one of the hydrogen atoms of the methylene group is substituted with a hydrocarbon-based group.

BACKGROUND INFORMATION

Methylenedioxybenzene is a product widely used in organic chemistry. It is used in particular as a synthesis intermediate in the pharmaceutical, agrochemical and perfumery fields.

Several synthetic pathways are described in the literature.

In particular, it is known practice to produce it according to a method which consists in reacting pyrocatechol (or 1,2-dihydroxybenzene) and methylene chloride in the presence of large amounts of sodium hydroxide and of a chain-transfer agent (FR 2 339 605).

This method suffers from many drawbacks. It is carried out under pressure, which involves special equipment.

It uses methylene chloride, which is a reactant that must be used with care. Exposure to the vapors can cause an irritation of the respiratory pathways (coughing), of the eyes, of the skin and of the digestive pathways, causing nausea and vomiting.

It also has the drawback of being accompanied by the production of saline waste containing large amounts of sodium chloride, which implies an additional cost for treating the residual wastewater.

The object of the present invention is to provide a method which makes it possible to overcome the abovementioned drawbacks.

BRIEF DESCRIPTION

A method for producing optionally substituted methylenedioxybenzene has now been found, and it is this which forms the subject of the present invention, which method is characterized in that it comprises the reaction:
of a catechol corresponding to formula (I)

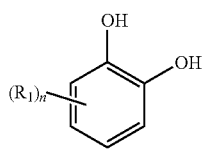

in which said formula:
$R_1$ symbolizes a substituent on the benzene ring, n, representing the number of substituents, is a number ranging from 0 to 4, preferably equal to 0 or 1,
and of an aldehyde of formula (II):

$$R-CHO \qquad (II)$$

in which said formula, R represents a hydrogen atom or a hydrocarbon-based group having from 1 to 12 carbon atoms,
the reaction being carried out in the presence of a solid acid catalyst chosen from: a titanium silicalite and a zeolite of the zeolite β type, that is doped with tin and/or titanium.

According to a first embodiment of the invention, the reaction is carried out in the vapor phase.

According to another embodiment of the invention, the reaction is carried out in the liquid phase.

In accordance with the method of the invention, an optionally substituted catechol and an aldehyde are reacted in the presence of a solid catalyst as defined.

The method of the invention applies particularly well to pyrocatechol, but is also suitable for the substituted catechols represented by formula (I).

As examples of catechols to which the method of the invention applies, mention may be made, inter alia, of those which correspond to formula (I) in which $R_1$ represents an alkyl group, an alkoxy group or a halogen atom, preferably a chlorine or fluorine atom.

As regards the aldehyde involved in the method of the invention, it corresponds in particular to formula (II) in which R represents an alkyl, cycloalkyl, aryl or arylalkyl group.

DETAIL DESCRIPTION

In the context of the invention, the term "alkyl" is intended to mean a linear or branched hydrocarbon-based chain having from 1 to 6 carbon atoms, and preferably from 1 to 4 carbon atoms.

Examples of preferred alkyl groups are in particular methyl, ethyl, propyl, isopropyl, butyl, isobutyl and t-butyl.

The term "cycloalkyl" is intended to mean a monocyclic, cyclic hydrocarbon-based group comprising from 3 to 8 carbon atoms, preferably a cyclopentyl or cyclohexyl group.

The term "aryl" is intended to mean a phenyl group or a phenyl group substituted with one or more (for example 3) substituents. For the definition of the substituents, reference will be made to the meaning of the group $R_1$.

The term "arylalkyl" is intended to mean a linear or branched hydrocarbon-based group bearing a monocyclic aromatic ring and comprising from 7 to 12 carbon atoms, preferably benzyl.

The term "alkoxy" is intended to mean an alkyloxy group comprising from 1 to 6 carbon atoms in the alkyl chain, and even more preferably from 1 to 4 atoms.

The substituted catechols preferentially used in the method of the invention correspond to formula (I) in which $R_1$ represents an alkyl group having from 1 to 4 carbon atoms, preferably a methyl or tert-butyl group.

As preferred examples of catechols, mention may be made of pyrocatechol, 4-methylcatechol, 4-tert-butylcatechol and 2,4-di-tert-butylcatechol, preferably pyrocatechol.

As regards the aldehydes corresponding to formula (II), aliphatic aldehydes are preferably chosen, and in particular formaldehyde, acetaldehyde, propionaldehyde, butyraldehyde or benzaldehyde.

Acetaldehyde or any source of acetaldehyde, such as paraldehyde, can be used.

The reactant of choice is formaldehyde or any formaldehyde-generating agent. Use may be made of formaldehyde or any formaldehyde-generating agent, such as, for example, trioxane or paraformaldehyde used in the form of linear polyformaldehydes with an indifferent degree of polymerization, preferably having a number of ($CH_2O$) units of between 8 and 100 units.

Hexamethylenetetramine can also be used.

Trioxane is preferentially chosen.

The amount of aldehyde, expressed in moles of aldehyde per mole of catechol, can vary to a large extent. The catechol/aldehyde molar ratio can range between 1 and 5, and is preferably in the region of 3.

As regards the nature of the catalyst involved in the method of the invention, use is made of zeolitic type catalysts, i.e. a titanium silicalite and a zeolite β that is doped.

The present method involves a titanium silicalite which is a known zeolite described in the literature, in particular in "Atlas of zeolite structure types by W. M. Meier and D. H. Olson published by the Structure Commission of the International Zeolite Association (1992), p. 138."

The composition of the zeolite can be represented by the general formula:

$$x\ TiO_2, (1-x)SiO_2 \tag{I}$$

in which x is between 0.0001 and 0.5, preferably between 0.001 and 0.05.

Titanium silicalites (or TS-1), which have a crystalline structure similar to ZSM-5 and which are generically referred to as "pentasile-type" are preferentially used.

Their properties are described in the literature: B. Notari, Structure-Activity and Selectivity Relationship in Heterogeneous Catalysis, R. K. Grasselli and A. W. Sleight Editors, Elsevier, 1991, p. 243-256.

The preparation of this zeolite can be carried out according to the methods described in particular in FR-A-2 471 950 and FR-A-2 489 816, or according to the method used by M. A. Uguina et al. described in J. Chem. Soc. Chem. Commun. p. 27 (1994).

The method according to FR-A-2 471 950 and FR-A-2 489 816 generally comprises the preparation of a reaction mixture consisting of sources of silicon oxide and of titanium oxide, and, optionally, an alkali metal oxide, a nitrogenous organic base and water, having a composition in a molar ratio of reactants below:

$SiO_2/TiO_2$: 5 to 200, preferably 35 to 65,
$OH^-/SiO_2$: 0.1 to 1, preferably 0.03 to 0.6,
$H_2O/SiO_2$: 20 to 200, preferably 60 to 100,
$Me/SiO_2$: 0 to 0.5, preferably 0,
$RN^+/SiO_2$: 0.1 to 2, preferably 0.4 to 1, in said ratios, Me represents an alkali metal ion, preferably sodium or potassium, and $RN^+$ represents a nitrogenous organic base.

The source of silicon oxide can be a tetraalkyl orthosilicate, preferably tetraethyl orthosilicate, or a silica in colloidal form or else an alkali metal, preferably sodium or potassium, silicate.

The source of titanium oxide is a hydrolyzable titanium compound, preferably chosen from $TiCl_4$, $TiOCl_2$ and $Ti(alkoxy)_4$, preferably $Ti(OC_2H_5)_4$.

The organic base is chosen from quaternary ammonium hydroxides, preferably tetraalkylammonium hydroxides, and more particularly tetrapropylammonium hydroxide and tetrabutylammonium hydroxide, or else from amines such as, in particular, dipropylamine, tripropylamine, dibutylamine or tributylamine.

The reaction mixture is subjected to a hydrothermal treatment, in an autoclave at a temperature of between 130° C and 200° C., under its own pressure, for a period of 2 to 30 days, until the crystals of the zeolite precursor are formed.

These crystals are separated from the stock solution, carefully washed with water, and dried and heated for 1 hour to 72 hours, at 550° C., in the air.

The titanium silicalite thus obtained has the composition x $TiO_2$, $(1-x)SiO_2$ as described above.

The method used by M. A. Uguina et al. comprises the production of an amorphous dried cogel obtained by controlled hydrolysis of silicon alkoxides and titanium alkoxides (tetraethylorthosilicate and tetrabutyl-orthotitanate), and then impregnation of this cogel with an organic base (tetrapropylammonium hydroxide) followed by hydrothermal crystallization.

Firstly, a $TiO_2$—$SiO_2$ cogel is produced according to a preferred method of preparation, which consists in hydrolyzing, in an acidic medium, a source of silicon and then in adding a source of titanium. The sol thus prepared is gelled by adding a base or by heating. The gel is dried at an appropriate temperature.

The $TiO_2/SiO_2$ molar ratio in this cogel is preferably between 5 and 200, more preferably between 35 and 65.

The source of silicon is hydrolyzed in an acidic solution (for example, dilute HCl) and then the source of titanium is added.

The hydrolytic process is preferably carried out at ambient temperature.

Coprecipitation of the $TiO_2$—$SiO_2$ is obtained by adding a base, which can be $NH_4OH$, but use is preferably made of a tetraalkylammonium hydroxide, which also plays the role of structuring agent, and more particularly of tetrapropylammonium hydroxide or tetrabutylammonium hydroxide.

The cogel is dried, for example, overnight at 110° C.

The dried cogel is impregnated using a solution comprising the mobilizing agent as mentioned above, and then, after impregnation, the reaction mixture is crystallized.

The composition of the reaction mixture is characterized by a low water content, $H_2O/SiO_2$: 3 and 10, preferably in the region of 4,
$OH^-/SiO_2$: 0.1 to 1, preferably 0.03 to 0.6,
$RN^+/SiO_2$: 0.1 to 2, preferably 0.2 to 1;

in said ratio, $RN^+$ represents the organic structuring agent.

The crystallization of the zeolite can be obtained by heating the cogel for the period of time necessary for crystallization, according to the conventional procedure for synthesizing zeolite well known to those skilled in the art, for example 24 hours at 170° C.

At the end of hydrothermal treatment, the product obtained is separated according to conventional solid/liquid separation techniques, preferably by filtration.

It is washed, preferably with distilled water, and is then subjected to drying at a temperature, for example, of 110° C. and then to calcination, for example 550° C., for 3 hours.

An MFI-type titanium silicalite is obtained, which can be used in the method of the invention It advantageously exhibits an infrared absorption band at 950-960 $cm^{-1}$.

It is also possible to use an MFI-type titanium silicalite which is prepared in a fluoride medium. In this case, the titanium silicalite is called "titanozeosilite". Thus, use can in particular be made of the MFI-type titanozeosilite which is the subject of WO 00/23185.

Titanozeosilite has an orthorhombic crystalline system and contains fluorine, the fluorine concentration, after calcination, being advantageously between 0.01 and 0.8%. The crystals obtained are in the form of prismatic rods having the following average size: thickness between 0.1 and 5 µm, preferably between 0.2 and 1 µm; length between 0.5 and 20 µm, preferably between 1 and 5 µm; width between 0.3 and 15 µm, preferably between 0.5 and 2.5 µm.

It is also possible to make use of an MEL-type or TS-2 type titanium silicalite. Thus, use may in particular be made of the MEL-type silicalite which is the subject of WO 00/23377.

Titanium silicalite has a quadratic crystalline system. The crystals are in the form of parallelepipeds having the following average size: thickness between 50 and 500 nm, preferably between 100 and 250 nm; length between 100 and 1000 nm, preferably between 300 and 500 nm; width between 50 and 500 nm, preferably between 100 and 250 nm.

Another type of catalyst suitable for the invention, which is described in WO 03/064363 is a microporous molecular sieve of zeolite β type, in which some of the silicon atoms are substituted with tin and/or titanium and/or aluminum.

The catalyst involved in the method of the invention corresponds to an empirical formula, after calcination, which is as follows:

$$(Al_w Si_{1-y-z} Sn_y Ti_z)O_2 \quad (II)$$

in which said formula (II):
w is a number between 0 and 0.2, preferably between 0 and 0.1,
y is a number between 0 and 0.1,
z is a number between 0 and 0.1,
y and z cannot be simultaneously equal to 0.

The zeolitic catalysts are microporous solids, the pore size of which generally ranges between 5 and 7 Å, and preferably between 5.6 and 6.6 Å.

A first variant of the method of the invention consists in using a microporous molecular sieve of tin zeolite β type.

Another variant of the method of the invention is to make use of a microporous molecular sieve of the type zeolite β comprising Ti or Ti+Al.

A catalyst that is suitable for implementing the method of the invention is a microporous molecular sieve of tin zeolite β type corresponding to an empirical formula, after calcination, which is as follows:

$$[Si_{1-y} Sn_y]O_2 \quad (IIA)$$

in which said formula (IIA), y is between 0.001 and 0.1, preferably between 0.001 and 0.05.

Said catalyst is known and is described in particular in EP-A 1 010 667.

Another type of catalyst that is suitable for the invention is a microporous molecular sieve of titanium zeolite β type corresponding to an empirical formula, after calcination, which is as follows:

$$[Si_{1-z} Ti_z]O_2 \quad (IIB)$$

in which said formula (IIB), z is between 0.001 and 0.1.

A method for producing such a catalyst is described by T. Blasco et al. [J. Phys. Chem. B, 102, 75, 1998].

It is also possible to make use of a titanium catalyst comprising silicon and aluminum, which can be represented by the empirical formula, after calcination, which is as follows:

$$(Al_w Si_{1-z} Ti_z)O_2 \quad (IIC)$$

in which said formula (IIC):
w is a number greater than 0, between 0 and 0.2, preferably between 0.001 and 0.1,
z is a number between 0.001 and 0.1.

For the production of said catalyst, reference may be made to the works by T. Blasco et al., J. Am. Chem. Soc., 115, (1993), p. 11 806-11 813.

When the catalyst is of zeolitic type, it can be used in the form of a powder, granules, chips, beads, pellets or in extruded form, etc.

The zeolite formulated is preferably formulated according to the extrusion technique.

Among the various catalysts mentioned above, MFI-type titanium silicalite (or TS-1) is preferred.

In accordance with the invention, the method is carried out in the gas phase. This expression is intended to mean that the various reactants are vaporized under the reaction conditions, but the method does not exclude the presence of a possible liquid phase resulting either from the physical properties of the reactants, or from an implementation under pressure or the use of an organic solvent.

The gas-phase method is the preferred embodiment of the invention.

The vector gas is optional and is in general a gas or a mixture of gases that are not reactive under the reaction conditions. Gases such as nitrogen, air, argon or helium can be used. Advantageously, the ratio by volume of the vector gas to the two reactants ranges between 0 and 10, preferably between 0.1 and 2.0.

The temperature of the condensation reaction is generally between 200° C. and 500° C., and preferably between 250° C. and 450° C., and even more preferably between 300° C. and 380° C.

The reaction pressure is preferably atmospheric pressure, but it is also possible to carry out the method under reduced pressure, which can be as low as 100 mm of mercury.

In accordance with the method of the invention, the starting reactants, i.e. the catechol and the aldehyde, preferably a source of formaldehyde, are vaporized. They are brought into contact with the catalyst, preferably entrained by means of a vector gas.

A variant of the invention consists in using a solvent for vaporizing the reactants. As examples of solvents that are suitable for the invention, mention may in particular be made of linear or cyclic, preferably aliphatic or cycloaliphatic, ether oxides, in particular dimethoxyethane, dioxane or tetrahydrofuran. The amount used is defined such that the reactants are solubilized at ambient temperature.

The contact time, which is defined as the ratio of the apparent volume of catalyst to the flow rate of the gas stream (which includes the vector gas), can vary to a large extent, and is most commonly between 0.2 and 50 seconds. The contact time is preferably chosen between 0.4 and 10 seconds.

As regards the practical realization of the invention, the first step is the production of the catalytic bed, which consists of the catalytic active phase deposited on a support (for example, sintered glass or screen), which allows the gases to circulate without elution of the catalyst. The reactants are subsequently used and several variants are possible.

It is possible to vaporize each of the reactants, in different chambers, and then to perform the mixing in a mixing chamber and to introduce the resulting gas stream over the catalyst. The vector gas can be introduced in parallel with said gas stream or else in the mixing chamber.

Another variant consists in producing a solution. comprising the reactants, and then in vaporizing said mixture and in introducing it onto the catalyst, in parallel with the vector gas.

Another embodiment of the invention is to make use of an organic solvent which is inert under the reaction conditions and which is chosen such that it solubilizes the two reactants.

Thus, an organic solution comprising the reactants is produced, and then said mixture is vaporized and introduced onto the catalyst, in parallel with the vector gas.

At the end of the reaction, all the gases are condensed and the reactants that have not reacted are separated from the products obtained, by distillation.

Another variant of the method of the invention consists in carrying out the reaction in the liquid phase.

In this case, an organic solvent is used.

The choice of the organic solvent is such that it must meet certain requirements.

It must be inert under the reaction conditions.

It must solubilize the two reactants and the product obtained, i.e. the optionally substituted methylenedioxybenzene.

As examples of solvents, use is made of the ether oxides as mentioned above.

From a practical point of view, the catalyst, preferably in powdered form, the organic solvent and the reactants are loaded into a reactor and heated under autogenic pressure from the reactants and solvent.

The temperature generally ranges between 100° C. and 200° C., preferably between 120° C. and 150° C.

At the end of the reaction, the optionally substituted methylenedioxybenzene is obtained, which can be represented by the formula below:

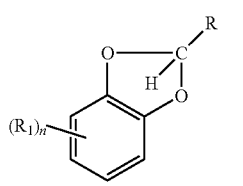

(III)

in which said formula, R, $R_1$ and n have the meaning given above.

At the end of the reaction, the catalyst is separated by a solid/liquid separation technique, preferably by filtration.

The optionally substituted methylenedioxybenzene is recovered from the liquid phase, preferably by distillation.

The present method is most particularly suitable for a continuous implementation.

An example of realization of the invention is given hereinafter, and is given by way of illustration which is in no way limiting in nature.

In the examples, the yield (RR) is defined as the ratio of the number of moles of product formed to the number of moles of substrate involved.

EXAMPLE 1

5 ml of powdered glass, 4 ml of TS-1 (i.e. 2.2 g) and 5 ml of powdered glass are successively introduced into a glass gas-phase reactor with an internal diameter of 21 mm and equipped with a temperature probe.

The catalytic bed is heated to 330° C. under a stream of nitrogen of 2 l/h.

A solution having the following composition is prepared:
dioxane: 45 g
pyrocatechol: 15 g (136 mmol)
trioxane: 1.36 g (15.1 mmol, i.e. 45.3 mmol of formaldehyde)

This solution is injected at a rate of 4 ml/h, for 5 hours, i.e. 22.8 g of solution injected.

The condensates are subsequently recovered and the methylenedioxybenzene formed is quantitatively determined by high performance liquid chromatography.

A methylenedioxybenzene yield of 28%, relative to the HCHO units injected, is obtained.

EXAMPLE 2

Example 1 is reproduced, the only difference being that the TS-1 is replaced with TS-2.

A methylenedioxybenzene yield of 30%, relative to the HCHO units injected, is obtained.

EXAMPLE 3

Example 1 is reproduced, the only difference being that the pyrocatechol is replaced with 4-methylcatechol.

A 4-methylmethylenedioxybenzene yield of 30%, relative to the HCHO units injected, is obtained.

EXAMPLE 4

Paraldehyde is used in this example.

5 ml of powdered glass, 4 ml of TS-1 (i.e. 2.2 g) and 5 ml of powdered glass are successively introduced into a glass reactor having an internal diameter of 21 mm and equipped with a temperature probe.

The catalytic bed is heated to 330° C. under a stream of nitrogen of 2 l/h.

A solution composed of 45 g of dioxane, 15 g of pyrocatechol and 2 g of paraldehyde is prepared.

This solution is injected at a rate of 4 ml/h, for 5 hours, i.e. 23 g of solution injected.

The condensates are recovered and the product formed is quantitatively determined.

A 2-methyl-1,3-benzodioxole yield of 51%, relative to the $CH_3CHO$ units introduced, is calculated.

EXAMPLE 5

Propionaldehyde is used in this example.

5 ml of powdered glass, 4 ml of TS-1 (i.e. 2.2 g) and 5 ml of powdered glass are successively introduced into a glass reactor having an internal diameter of 21 mm and equipped with a temperature probe.

The catalytic bed is heated to 330° C. under a stream of nitrogen of 2 l/h.

A solution composed of 45 g of dioxane, 15 g of pyrocatechol and 2.7 g of propionaldehyde is prepared.

This solution is injected at a rate of 4 ml/h, for 5 hours, i.e. 25 g of solution injected.

The condensates are recovered and the product formed is quantitatively determined.

A 2-ethyl-1,3-benzodioxole yield of 51%, relative to the $CH_3CH_2CHO$ introduced, is calculated.

EXAMPLE 6

Benzaldehyde is used in this example.

5 ml of powdered glass, 4 ml of TS-1 (i.e. 2.2 g) and 5 ml of powdered glass are successively introduced into a glass reactor having an internal diameter of 21 mm and equipped with a temperature probe.

The catalytic bed is heated to 330° C. under a stream of nitrogen of 2 l/h.

A solution composed of 45 g of dioxane, 15 g of pyrocatechol and 4.8 g of benzaldehyde is prepared.

This solution is injected at a rate of 4 ml/h, for 5 hours, i.e. 24 g of solution injected.

The condensates are recovered and the product formed is quantitatively determined.

A 2-phenyl-1,3-benzodioxole yield of 18%, relative to the benzaldehyde introduced, is calculated.

EXAMPLE 7

4-Methylcatechol and trioxane are used in this example.

5 ml of powdered glass, 4 ml of TS-1 (i.e. 2.2 g) and 5 ml of powdered glass are successively introduced into a glass reactor having an internal diameter of 21 mm and equipped with a temperature probe.

The catalytic bed is heated to 330° C. under a stream of nitrogen of 2 l/h.

A solution composed of 45 g of dioxane, 16.9 g of 4-methylcatechol and 1.4 g of trioxane is prepared.

This solution is injected at a rate of 4 ml/h, for 5 hours, i.e. 23 g of solution injected.

The condensates are recovered and the product formed is quantitatively determined.

A 5-methyl-1,3-benzodioxole yield of 34%, relative to the HCHO units introduced, is calculated.

The invention claimed is:

1. A method for producing optionally substituted methylenedioxybenzene, comprising the steps of:

reacting a catechol corresponding to formula (I):

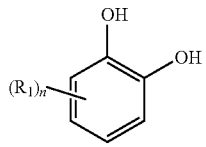

(I)

wherein:
R$_1$ represents a substituent on the benzene ring,
n, representing the number of substituents, is a number ranging from 0 to 4,
with an aldehyde of formula (II):

R—CHO    (II)

wherein, R represents a hydrogen atom or a hydrocarbon-based group having from 1 to 12 carbon atoms,
the reaction being carried out in the presence of a solid acid catalyst which is a titanium silicalite or a zeolite β, that is doped with tin and/or titanium.

2. The method as claimed in claim 1, wherein the catalyst is an MFI or MEL titanium silicalite.

3. The method as claimed in claim 1, wherein the catalyst is a doped zeolite β, which corresponds, after calcination, to the following empirical formula:

$(Al_wSi_{1-y-z}Sn_yTi_z)O_2$    (II)

wherein:
w is a number between 0 and 0.2,
y is a number between 0 and 0.1,
z is a number between 0 and 0.1, and
y and z cannot simultaneously be equal to 0.

4. The method as claimed in claim 3, wherein the catalyst is a tin zeolite β, which corresponds, after calcination, to the following empirical formula:

$[Si_{1-y}Sn_y]O_2$    (IIA)

wherein y is between 0.001 and 0.1.

5. The method as claimed in claim 3, wherein the catalyst is a titanium zeolite β, which corresponds, after calcination, to the following empirical formula:

$[Si_{1-z}Ti_z]O_2$    (IIB)

wherein z is between 0.001 and 0.1.

6. The method as claimed in claim 3, wherein the catalyst is a titanium zeolite β comprising silicon and aluminum, which corresponds, after calcination, to the following empirical formula:

$(Al_wSi_{1-z}Ti_z)O_2$    (IIC)

wherein:
w is a number greater than 0, between 0 and 0.2, and
z is a number between 0.001 and 0.1.

7. The method as claimed in claim 2, wherein the zeolite β is used in the form of a powder, granules, chips, beads, pellets or in extruded form.

8. The method as claimed in claim 1, wherein the catechol corresponds to formula (I) in which R$_1$ represents an alkyl group, an alkoxy group or a halogen atom.

9. The method as claimed in claim 8, wherein the catechol corresponds to formula (I) in which R$_1$ represents an alkyl group having from 1 to 4 carbon atoms.

10. The method as claimed in claim 9, wherein the catechol is pyrocatechol, 4-methylcatechol, 4-tert-butylcatechol or 2,4-di-tert-butylcatechol.

11. The method as claimed in claim 1, wherein the aldehyde corresponds to formula (II) in which R represents a hydrogen atom, or an alkyl, cycloalkyl, aryl or arylalkyl group.

12. The method as claimed in claim 11, wherein the aldehyde is formaldehyde, acetaldehyde or a source of acetaldehyde, paraldehyde, propionaldehyde, butyraldehyde or benzaldehyde.

13. The method as claimed in claim 11, wherein the aldehyde of formula (II) comprises formaldehyde or a formaldehyde-generating agent.

14. The method as claimed in claim 13, wherein the aldehyde of formula (II) comprises trioxane.

15. The method as claimed in claim 1, wherein catechol and aldehyde have a molar ratio catechol/aldehyde ranging between 1 and 5.

16. The method as claimed in claim 1 carried out in a gas phase.

17. The method as claimed in claim 16, wherein a vector gas or a mixture of gases which are not reactive under the reaction conditions is used.

18. The method as claimed in claim 17, wherein the vector gas and the two reactants have a ratio by volume of the vector gas to the two reactants ranging between 0 and 10.

19. The method as claimed in claim 16, wherein the condensation reaction is carried out at a temperature of between 200° C. and 500° C.

20. The method as claimed in claim 16, wherein the condensation reaction is carried out at atmospheric pressure.

21. The method as claimed in claim 16, carried out with a contact time, which is defined as the ratio of the apparent catalyst volume to the flow rate of the gas stream which includes the vector gas, of between 0.2 and 50 seconds.

22. The method as claimed in claim 16, wherein an organic solvent is used to vaporize the reactants.

23. The method as claimed in claim 22, wherein the organic solvent is dioxane.

24. The method as claimed in claim 16, wherein the starting reactants are brought into contact with the catalyst, the gases are condensed at the end of the reaction and the optionally substituted methylenedioxybenzene obtained is separated.

25. The method as claimed in claim 1, wherein the method is carried out in a liquid phase.

26. The method as claimed in claim 25, wherein the method is carried out at a temperature ranging between 100° C. and 200° C.

27. The method as claimed in claim 25, wherein the reaction is carried out in an organic solvent which is a linear or cyclic, aliphatic or cycloaliphatic ether oxide.

28. The method as claimed in claim 25, wherein the catalyst, the organic solvent and the reactants are loaded into a reactor and heated under autogenic pressure from the reactants and solvent, and then the optionally substituted methylenedioxybenzene obtained is recovered.

29. The method as claimed in claim 1, wherein in the formula (I), n is equal to 0 or 1.

30. The method as claimed in claim 2, wherein the catalyst is a TS-1 zeolite.

31. The method as claimed in claim 3, wherein in the formula (II), w is between 0 and 0.1.

32. The method as claimed in claim 4, wherein in the formula (IIA), y is between 0.001 and 0.05.

33. The method as claimed in claim 6, wherein in the formula (IIC), w is between 0.001 and 0.1.

34. The method as claimed in claim 8, wherein in the formula (I), $R_1$ represents a chlorine or fluorine atom.

35. The method as claimed in claim 9, wherein in the formula (I), $R_1$ represents a methyl or tert-butyl group.

36. The method as claimed in claim 10, wherein the catechol is pyrocatechol.

37. The method as claimed in claim 13, wherein the aldehyde of formula (II) comprises trioxane or paraformaldehyde.

38. The method as claimed in claim 13, wherein the aldehyde of formula (II) is in the form of a linear polyformaldehyde with an indifferent degree of polymerization, having a number of $(CH_2O)$ units of between 8 and 100 units, and the aldehyde is used with a hexamethylenetetramine.

39. The method as claimed in claim 15, wherein catechol and aldehyde have a molar ratio catechol/aldehyde of about 3.

40. The method as claimed in claim 17, wherein the vector gas or the mixture of gases which are not reactive under the reaction conditions, comprises nitrogen, air, argon or helium.

41. The method as claimed in claim 18, wherein the vector gas and the two reactants have a ratio by volume of the vector gas to the two reactants between 0.1 and 2.0.

42. The method as claimed in claim 19, wherein the condensation reaction is carried out at a temperature of between 300° C. and 380° C.

43. The method as claimed in claim 21, carried out with a contact time of between 0.4 and 10 seconds.

44. The method as claimed in claim 22, wherein the organic solvent comprises a linear or cyclic, aliphatic or cycloaliphatic ether oxide.

45. The method as claimed in claim 24, wherein the starting reactants are brought into contact with the catalyst, entrained by means of a vector gas.

46. The method as claimed in claim 26, wherein the method is carried out at a temperature ranging between 120° C. and 150° C.

47. The method as claimed in claim 28, wherein the catalyst is in powdered form.

* * * * *